(12) United States Patent
Burkhardt et al.

(10) Patent No.: US 7,731,898 B2
(45) Date of Patent: Jun. 8, 2010

(54) REAGENT CONTAINER ASSEMBLY AND ANALYZER COMPRISING SUCH ASSEMBLY

(75) Inventors: Claudius Burkhardt, Lucerne (CH); Gottlieb Schacher, Kriens (CH); Renato Belz, Emmenbrücke (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 734 days.

(21) Appl. No.: 11/523,842

(22) Filed: Sep. 20, 2006

(65) Prior Publication Data

US 2007/0128085 A1 Jun. 7, 2007

(30) Foreign Application Priority Data

Sep. 21, 2005 (EP) .................................. 05077155

(51) Int. Cl.
*G01N 35/00* (2006.01)
*G01N 35/10* (2006.01)
(52) U.S. Cl. ........................... 422/64; 422/63; 422/102; 422/104; 436/43; 436/45; 436/49
(58) Field of Classification Search ........................ None
See application file for complete search history.

(56) References Cited

U.S. PATENT DOCUMENTS

| 4,276,258 A | 6/1981 | Ginsberg et al. | |
|---|---|---|---|
| 5,171,531 A * | 12/1992 | Christianson et al. | 422/64 |
| 5,510,082 A | 4/1996 | Arai et al. | |
| 2003/0022380 A1 * | 1/2003 | Jakubowicz et al. | 436/54 |
| 2005/0123445 A1 * | 6/2005 | Blecka et al. | 422/64 |

FOREIGN PATENT DOCUMENTS

| EP | 0 510 686 A2 | 10/1992 |
|---|---|---|
| EP | 0 851 232 A1 | 7/1998 |

* cited by examiner

*Primary Examiner*—Kathryn Wright
(74) *Attorney, Agent, or Firm*—Dinsmore & Shohl LLP

(57) ABSTRACT

A reagent container assembly adapted for being installed in a cavity of an analyzer. The reagent container assembly comprises a housing having an upper opening and defining at least one circular array of chambers, each chamber being adapted for receiving a reagent container, a cover for closing the upper opening of the housing, and a locking mechanism arranged within the housing. The locking mechanism is adapted for locking the cover and for preventing rotation thereof. The locking mechanism is further adapted for locking the housing and thereby preventing rotation thereof when the reagent container assembly is removed from its position in the analyzer. The locking mechanism is further adapted for cooperating with a pin arranged at the bottom of the cavity of the analyzer when the reagent container assembly is installed in the analyzer, the housing being unlocked by the cooperation and thereby allowed to be rotated within the cavity of the analyzer.

15 Claims, 14 Drawing Sheets

REAGENT CONTAINER ASSEMBLY AND ANALYZER COMPRISING SUCH ASSEMBLY

RELATED APPLICATIONS

This application claims priority to EP 05077155.9 filed Sep. 21, 2005.

FIELD OF THE INVENTION

The invention concerns a reagent container assembly adapted for being installed in a substantially cylindrical cavity of an analyzer. The invention further concerns an analyzer comprising such a reagent container assembly.

BACKGROUND

In automatic analyzers, and in particular in clinical chemistry analyzers, it is convenient to have a reagent container assembly which contains a plurality of reagent containers suitable for carrying out various analysis and which can be easily handled and installed in the analyzer.

For proper and reliable operation of the analyzer it is indispensable to avoid using the wrong reagent when performing an analysis. It is therefore important to make sure that the proper reagents are loaded into the reagent container assembly installed in the analyzer and that the reagent management system of the analyzer has information that identifies those reagents. For this purpose, the individual reagent containers as well as the reagent container assemblies are identified e.g. by means of barcode labels for the purpose of automatic identification and control by the reagent management system of the analyzer.

In spite of the above actions and steps for ensuring proper identification and control of the reagents being used, it cannot be fully excluded that reagent containers installed in the analyzer are manually taken out and replaced by another reagent and that the reagent management system of the analyzer may fail to detect errors that may occur during such manipulations.

The problematic situation just mentioned is particularly prone to occur when the reagent container assemblies are manually handled for installing them into the analyzer and removing them from the analyzer when necessary. In larger analyzer systems, the risk of errors in handling reagents can be considerably reduced by an expensive, fully automatic handling of the regents. Such an approach is however not possible in case of a low cost, relatively small analyzer intended to be used in small laboratories or even by medical doctors in their own laboratories, because in those cases, in order to reduce the manufacturing costs of the analyzer, manual handling of the reagent assemblies is indicated. Nevertheless, also in those cases, it is desirable to reduce the risk of errors in handling the reagents as far as possible.

SUMMARY OF THE INVENTION

A first aim of the invention is to provide a reagent container assembly which makes possible to avoid the above-mentioned drawbacks of known reagent container assemblies.

According to a first aspect of the invention the above aim is achieved by means of a reagent container assembly adapted for being installed in a substantially cylindrical cavity of an analyzer, said reagent container assembly comprising a housing defining at least one circular array of chambers, each chamber being adapted for receiving a reagent container, said housing having an upper opening, a cover for closing said upper opening of said housing, and locking means arranged within said housing, said locking means comprising a locking sleeve and a locking pin, said locking means being adapted for locking said cover at all times, thereby preventing rotation of the cover with respect to the housing, said locking means being adapted for locking said housing and thereby preventing rotation of said housing when the reagent container assembly is removed from its position in said cavity of the analyzer, and said locking means being further adapted for cooperating with a bolt arranged at the center of the bottom of said cavity of the analyzer when the reagent container assembly is installed in the analyzer, said housing being unlocked by said cooperation and thereby allowed to be rotated within said cavity of the analyzer.

A second aim of the invention is to provide an analyzer that makes possible to avoid the above-mentioned drawbacks of analyzers known in the prior art.

According to a second aspect of the invention, the above aim is achieved by means of an automatic analytical apparatus comprising the reagent container assembly described above.

The main advantages obtained with a reagent assembly and an analyzer according to the invention is that the risk of errors in handling the reagents used is considerably reduced.

BRIEF DESCRIPTION OF THE DRAWINGS

The subject invention will now be described in terms of its preferred embodiments with reference to the accompanying drawings. These embodiments are set forth to aid the understanding of the invention, but are not to be construed as limiting.

Figure 15:
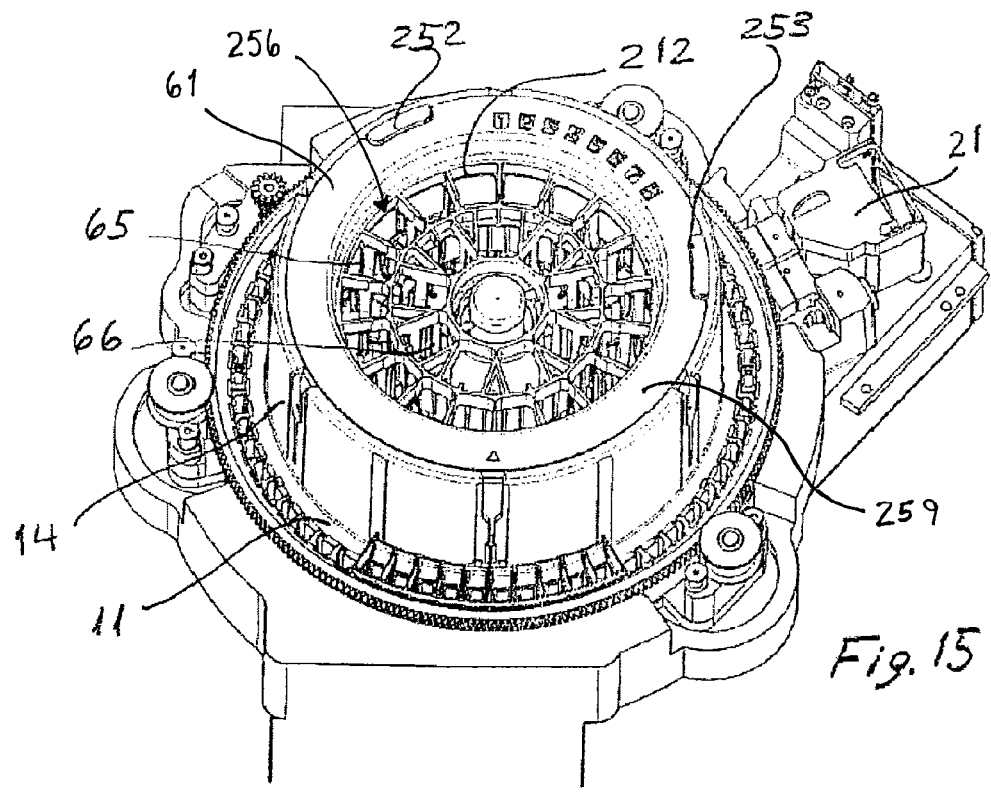
FIG. 15 shows a perspective view of reagent container assembly 61 installed in the analyzer, but without its cover and without any reagent container in it.
Figures 18, 19:
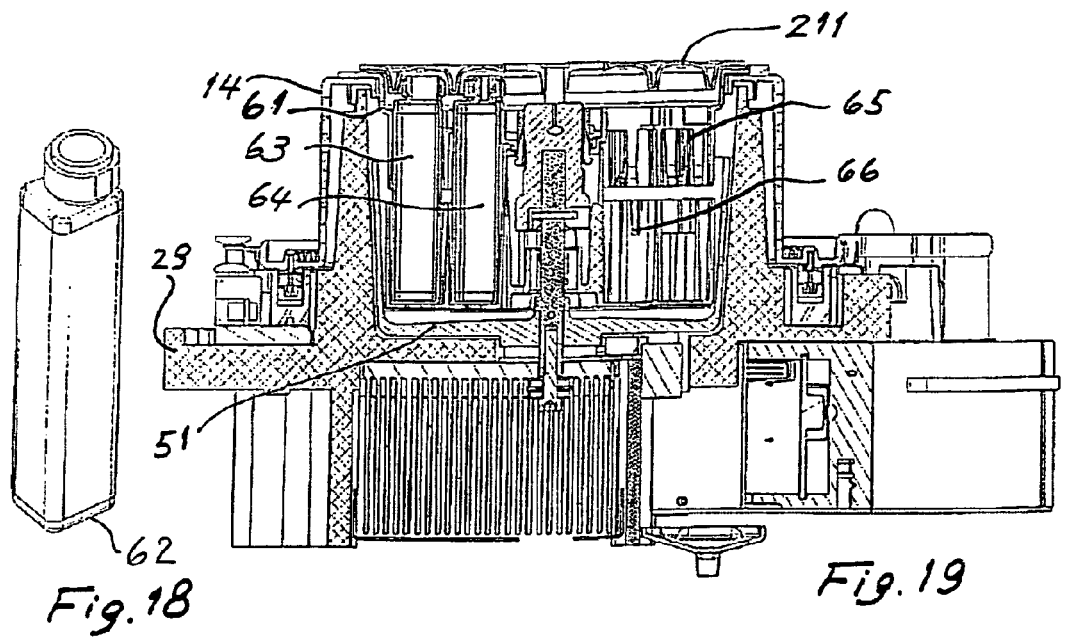
FIG. 18 shows a perspective view of a single reagent container.
FIG. 19 shows a cross-sectional view taken along a plane I-I in FIG. 17.
Figure 17:
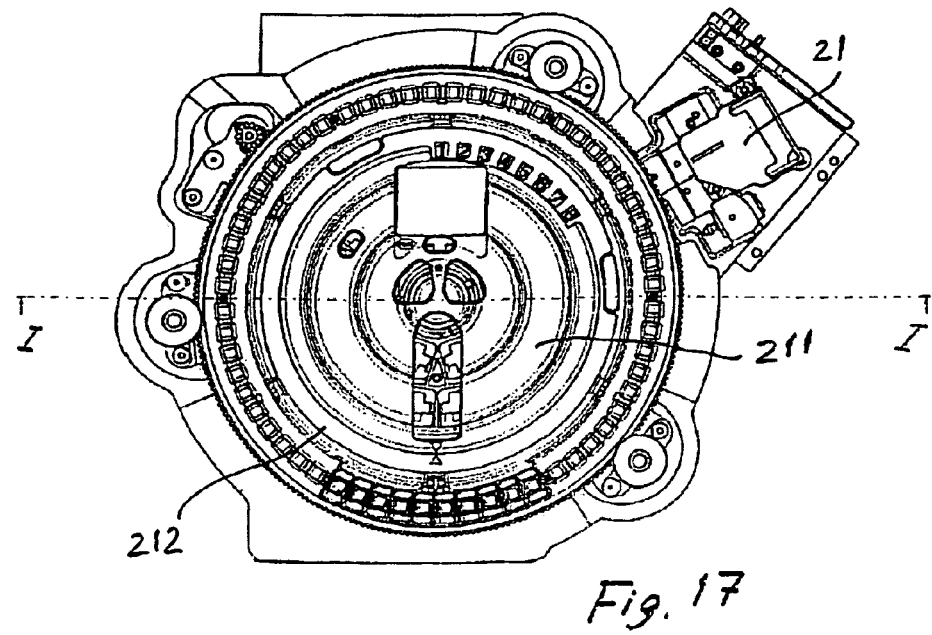
FIG. 17 shows a top view of the conveyor part of the analyzer shown in FIG. 1 and in particular reagent container assembly 61 before it is loaded with reagent containers.
Figure 27:
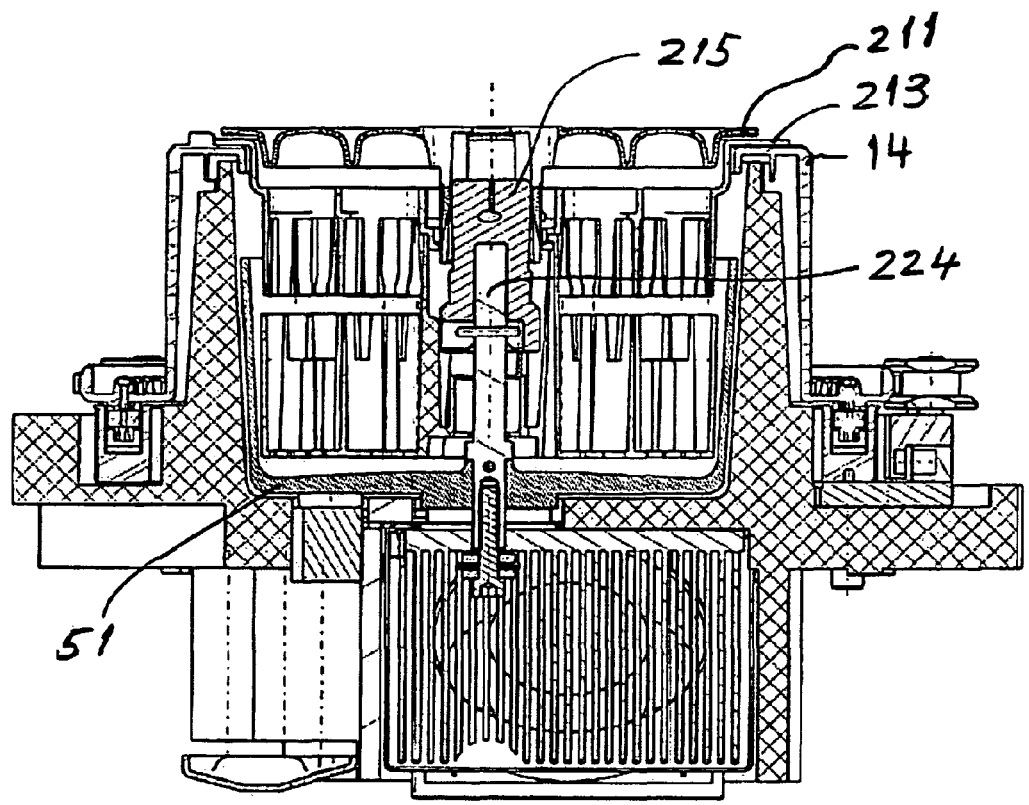
FIG. 27 shows a third cross-sectional view of reagent container assembly 61 taken along a plane M-M in FIG. 12. In this view the upper edge of housing upper part 213 rests on the top edge of second ring shaped body 14 of conveyor 11.
Figure 28:
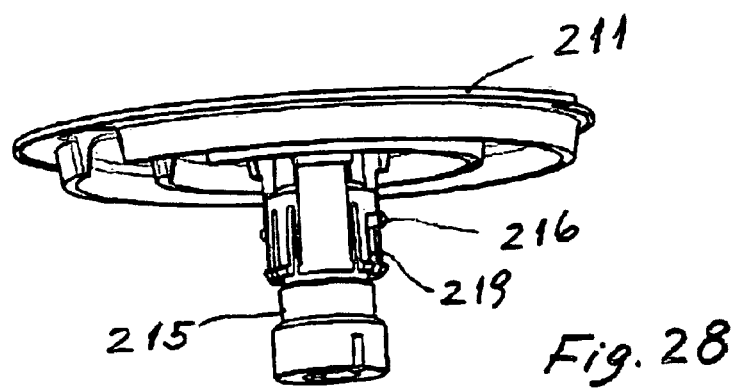
FIG. 28 shows a first perspective view of the cover 211 and of locking sleeve 215 in FIG. 27.
Figure 29:
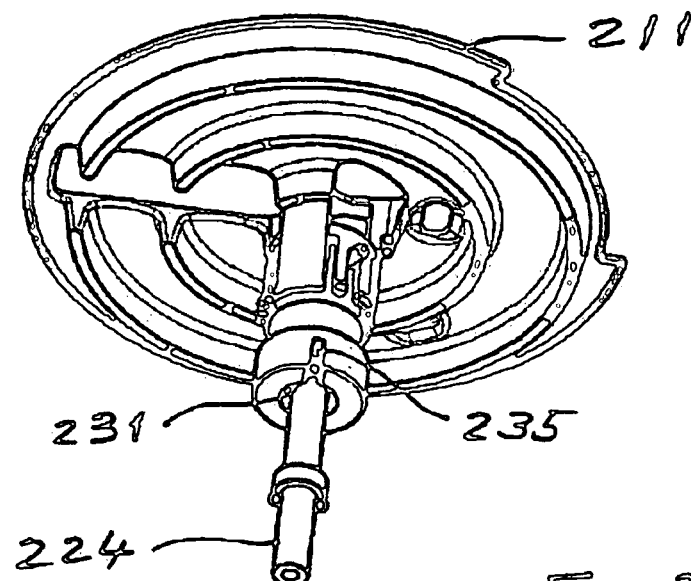
FIG. 29 shows a second perspective view of the cover 211, locking sleeve 215 and bolt 224 in FIG. 27.
Figure 30:
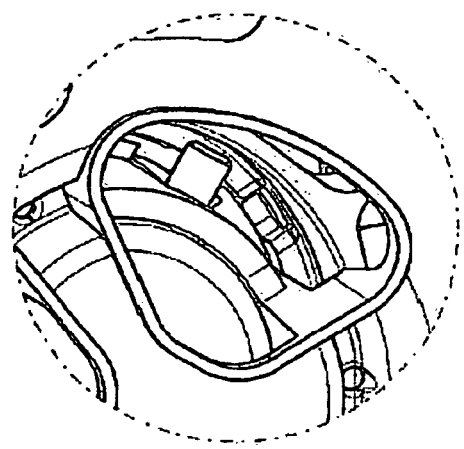
FIG. 30 shows a partial perspective view showing the position of locking pin 216 in the unlocked position of the housing 212.

REFERENCE NUMERALS IN DRAWINGS 11 conveyor
12 first ring shaped body
13 cavity for receiving a reaction cuvette
14 second ring shaped body
15 wall of second ring shaped body
16 opening
17 first chamber (within second ring shaped body)
18 sample tube area
19 cavity for receiving a sample tube
20 thermal block
21 photometer
22 rotor driving means
23 washing station
24 path of light beam of photometer
25 rotation axis of conveyor 11
26 portion of FIG. 15
27 portion of FIG. 17
28 portion of FIG. 19
29 thermal insulation layer
31 reaction cuvette
32 body of cuvette 31
33 lower end portion of cuvette 31
34 upper end portion of cuvette 31
35 bottom wall of cuvette 31
36 opening of cuvette 31
37 rigid tongue
38 rigid tongue
39 length symmetry axis of cuvette 31
40 flexible tongue
41 cuvette holder
42 body of cuvette holder
43 chamber of cuvette holder
44 connecting part/guiding rib
45 upper frame
46 lower frame
47 side wall
48 side wall
49 intermediate wall
50 flexible tongue
51 bucket/hollow body
52 bottom wall of bucket
53 side walls of bucket
54 second chamber within bucket
55 air gap
56 bottom wall of cavity 13
57 depression in inner surface of bottom wall 56
60 intermediate wall
60a intermediate wall
61 reagent container assembly
62 reagent container
63 reagent container
64 reagent container
65 chamber for receiving a reagent container
66 chamber for receiving a reagent container
71 automatic pipetting device
72 pipetting needle
73 rail of transport device of pipetting needle
211 cover
212 housing
213 upper part of housing
214 lower part of housing
215 locking sleeve
216 locking pin
217 recess (in upper part 213)
218 recess (in upper part 213)
219 guide (part of cover 211)
221 guide
222 guide
223 hook
224 bolt
225 air gap
226 recess
227 projection
228 projection
231 projection
232 projection
233 recess
234 recess
235 recess
236 recess
241 opening of cover 211 for pipetting operations
242 opening of cover 211 for pipetting operations
243 opening of cover 211 for gripping it by hand
244 opening of cover 211 for gripping it by hand
245 opening of cover 211 for removing or introducing a reagent container 251 upper surface of body 14
252 projection
253 projection
254 recess
255 recess

DETAILED DESCRIPTION OF THE INVENTION

Preferred embodiments are described hereinafter with reference to the accompanying drawings.

Example of an Analyzer

Figure 1:
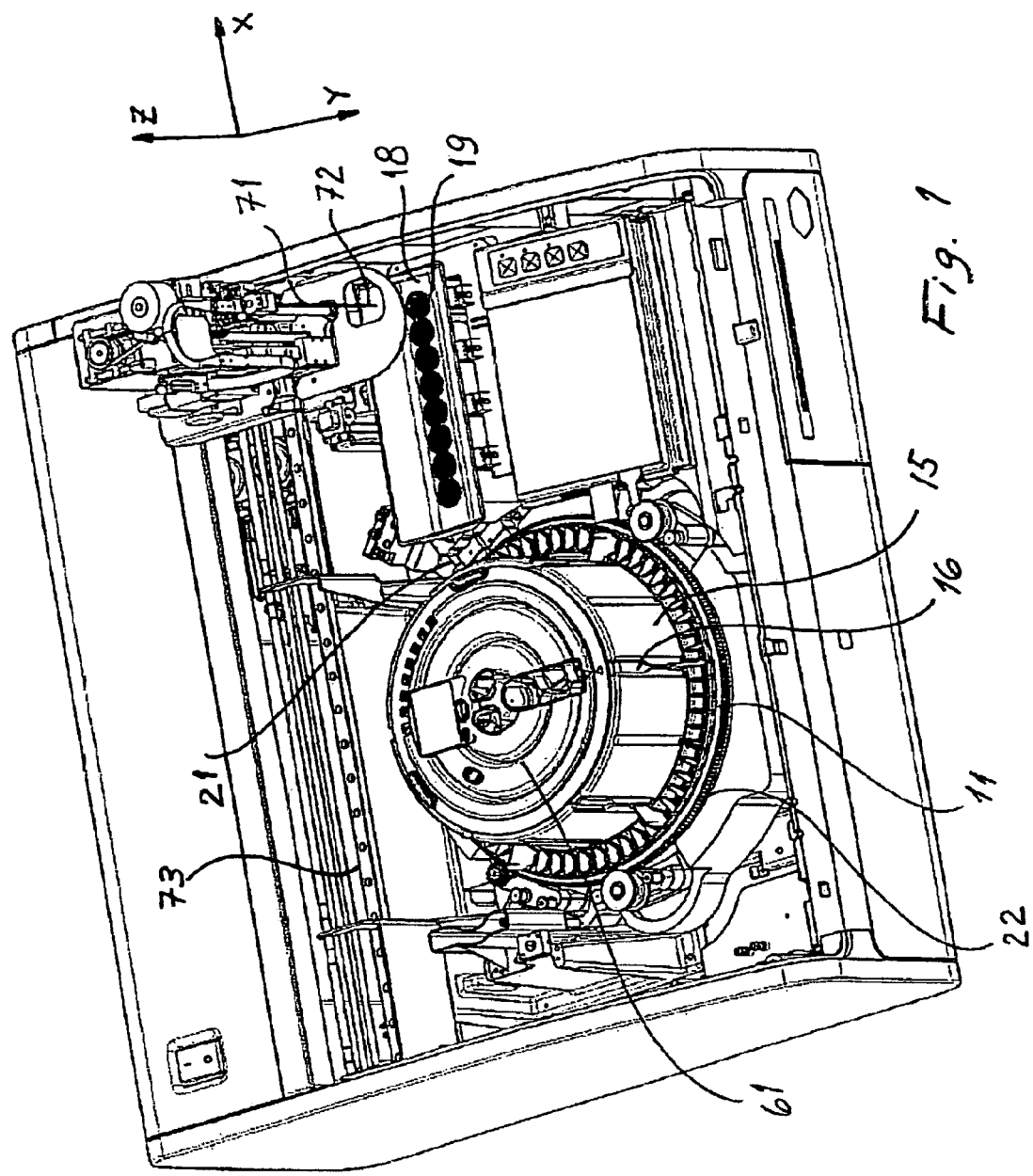
FIG. 1 shows a perspective view of an analyzer according to the invention.

As shown by FIG. 1 an analyzer according to the invention, e.g. a clinical-chemistry for analyzing sample-reagent mixtures contained in reaction cuvettes. The analyzer shown in FIG. 1 comprises a rotatable conveyor 11 for conveying reaction cuvettes 31 inserted in corresponding cavities of that conveyor along a circular path, at least one array of reaction cuvettes 31, a bucket or hollow body 51 (shown in FIG. 14) arranged in the central part of conveyor, a reagent container assembly 61 installed in a cavity 54 of hollow body 51, a sample tube area 18 located adjacent to conveyor 11, an automatic pipetting device 71, a photometer 21 located adjacent to conveyor 11, and conveyor driving means 22 for rotating conveyor 11.

Figure 3:
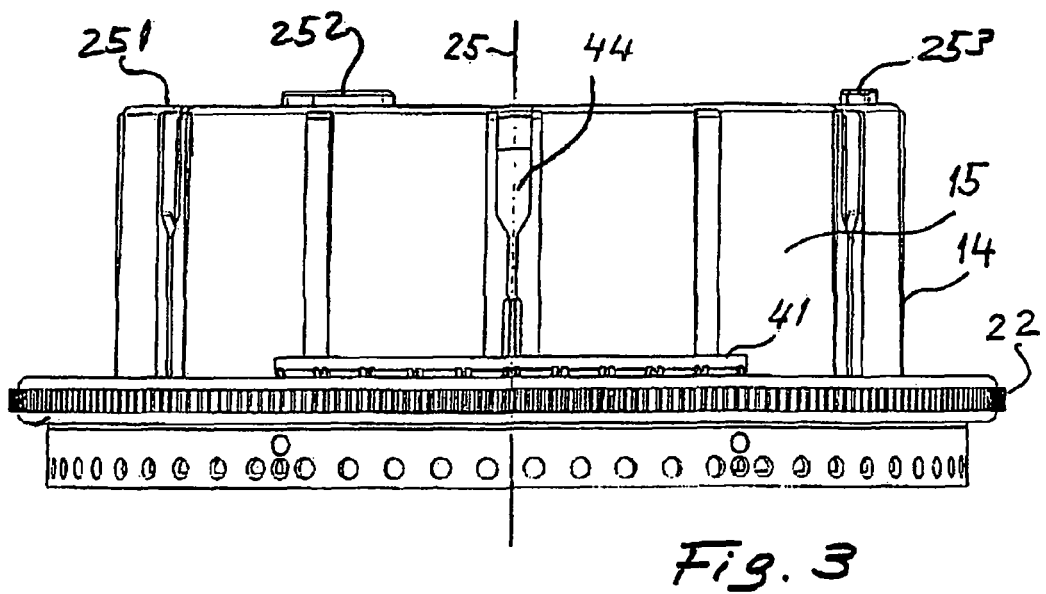
FIG. 3 shows a side view of conveyor 11 in FIG. 1.

FIG. 3 shows the rotation axis 25 of conveyor 11.

Reaction cuvettes 31 inserted in the above mentioned cavities of conveyor 11 are loosely held by a cuvette holder 41 described hereinafter in particular with reference to FIGS. 4 to 7. Such a cuvette holder 41 loosely holds a plurality of reaction cuvettes 31. A cuvette holder 41 and reaction cuvettes 31 held by cuvette holder 41 form a cuvette array. The analyzer comprises at least one such array. Usually reaction cuvettes of a plurality of such cuvette arrays are installed in corresponding cavities of conveyor 11. In the example shown by FIG. 1, conveyor 11 has cavities for receiving 60 reaction cuvettes distributed in 6 cuvette arrays each array having 10 reaction cuvettes.

Figure 2:
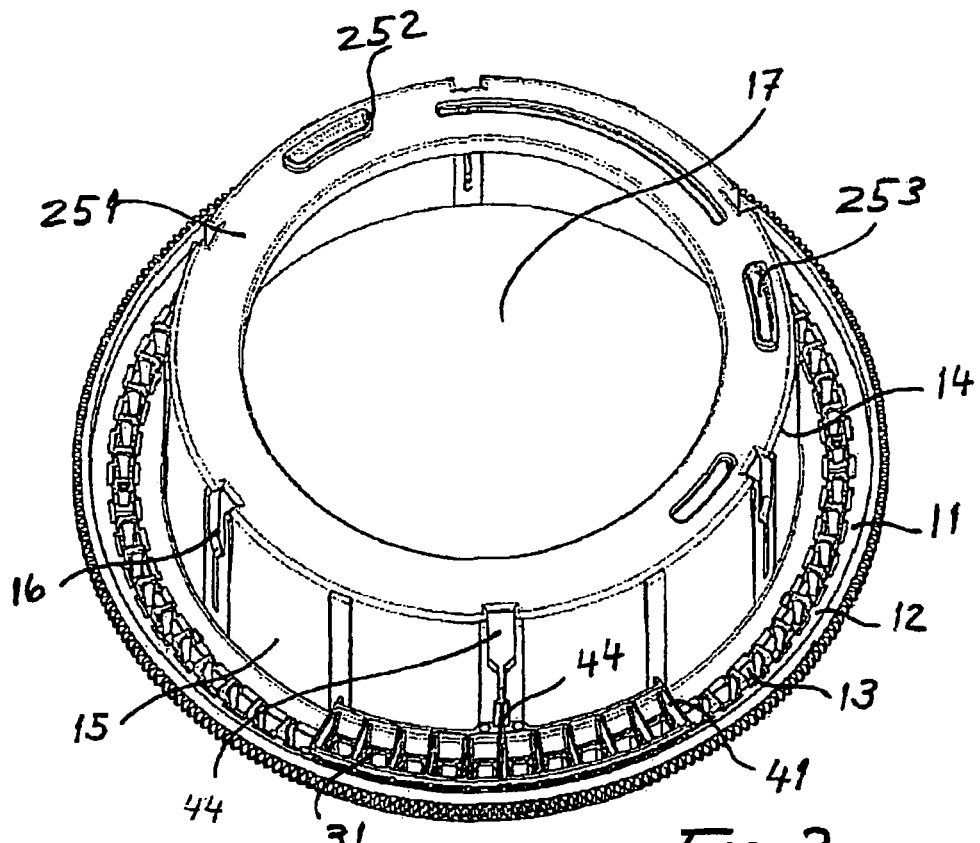
FIG. 2 shows a perspective view of conveyor 11 in FIG. 1.

Cuvette holder 41 serves for holding an array of reaction cuvettes 31. Cuvette holder 41 has a connecting part 44 which is adapted for inserting it into an opening 16 of wall 15 of the conveyor, thereby connecting cuvette holder 41 to conveyor 11. As shown by FIG. 2, the relative position of the connecting part 44 and the opening 16 of wall 15 are such that when connecting part 44 is inserted into opening 16 the reaction cuvettes 31 held by a cuvette holder 41 are inserted into corresponding cavities 13 of a first ring shaped body 12 of conveyor 11.

As shown by FIGS. 2 and 3, conveyor 11 comprises a first ring shaped body 12 and a second ring shaped body 14. First ring shaped body 12 has a circular array of cavities 13, each of which is adapted for receiving a single reaction cuvette 31 of the type described below with reference to FIGS. 8 to 10. First ring shaped body 12 is preferably made of a suitable metal.

Second ring shaped body 14 has a wall 15 which extends upwardly from the inner side of first ring shaped body 12. Wall 15 has openings 16, each of which is adapted for receiving a corresponding connecting part 44 of a cuvette holder 41. Second ring shaped body 14 defines a chamber 17 within the interior of body 14.

Second ring shaped body 14 has an upper ring shaped surface 251 which extends substantially in a horizontal plane and which has projections 252, 253 intended to engage corresponding recesses of a reagent container assembly described hereinafter.

Figure 14:
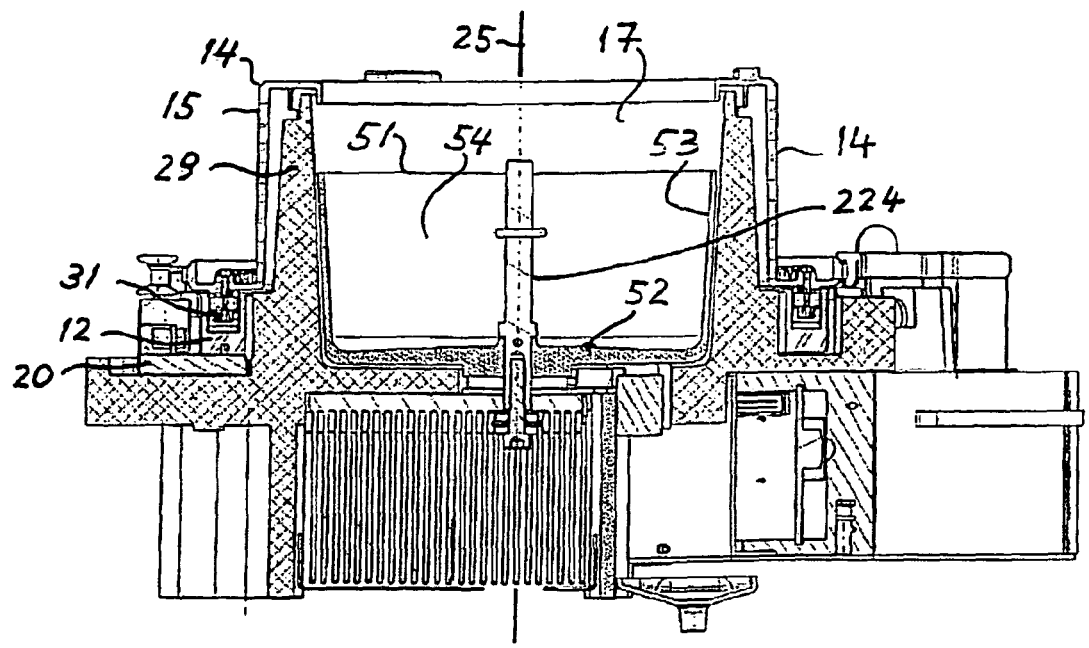
FIG. 14 shows a cross-sectional view taken along a plane H-H in FIG. 13.
Figure 13:
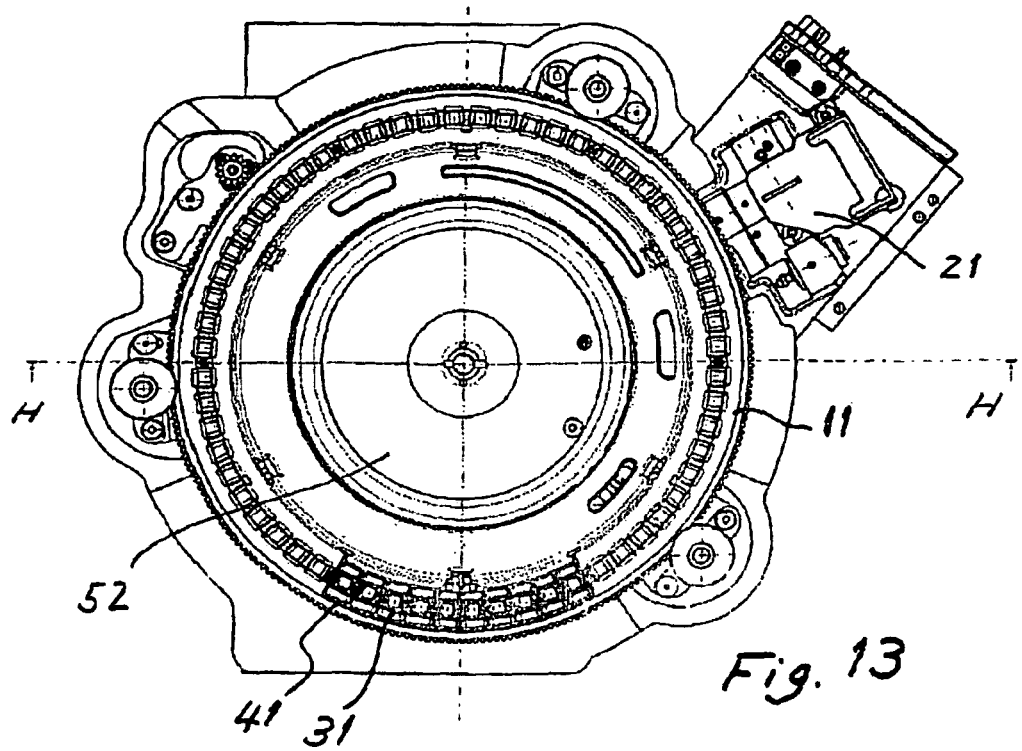
FIG. 13 shows a top view of the conveyor part of the analyzer shown in FIG. 1 when reagent container assembly 61 is removed therefrom.

FIG. 13 shows a top view of the conveyor part of the analyzer shown in FIG. 1 when reagent container assembly 61 is removed therefrom. FIG. 14 shows a cross-sectional view taken along a plane H-H in FIG. 13.

As shown by FIG. 14 a hollow body 51 is arranged in chamber 17 within second ring shaped body 14. Hollow body 51 has e.g. the shape of a bucket, and has a bottom wall 52 and side walls 53 which define a chamber 54.

Figure 11:
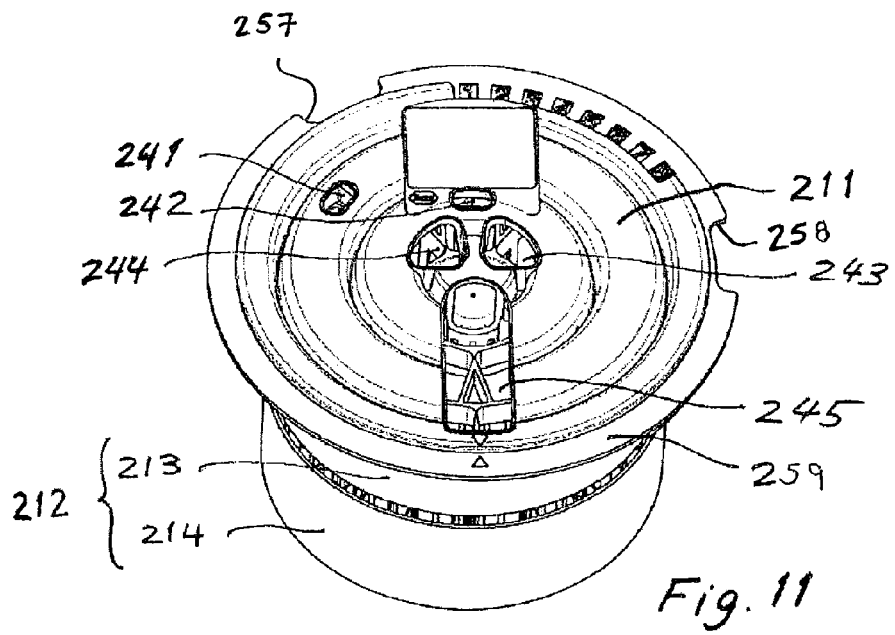
FIG. 11 shows a perspective view of reagent container assembly 61 when it is removed from the analyzer shown in FIG. 1.

FIG. 11 shows a perspective view of reagent container assembly 61 when it is removed from the analyzer shown in FIG. 1. Reagent container assembly 61 is adapted for being positioned with its lower part in chamber 54 of hollow body 51.

FIG. 15 shows a perspective view of reagent container assembly 61 installed in the analyzer, but without its cover and without any reagent container in it. FIG. 15 shows that when reagent container assembly 61 is installed in the analyzer, projections 252, 253 of the second ring shaped body 14 of conveyor 11 engage corresponding recesses in the upper flat edge of housing 212 and thereby connect housing to conveyor 11, so that when conveyor is rotated the housing 212 of reagent container assembly 61 rotates with conveyor 11.

Figure 16:
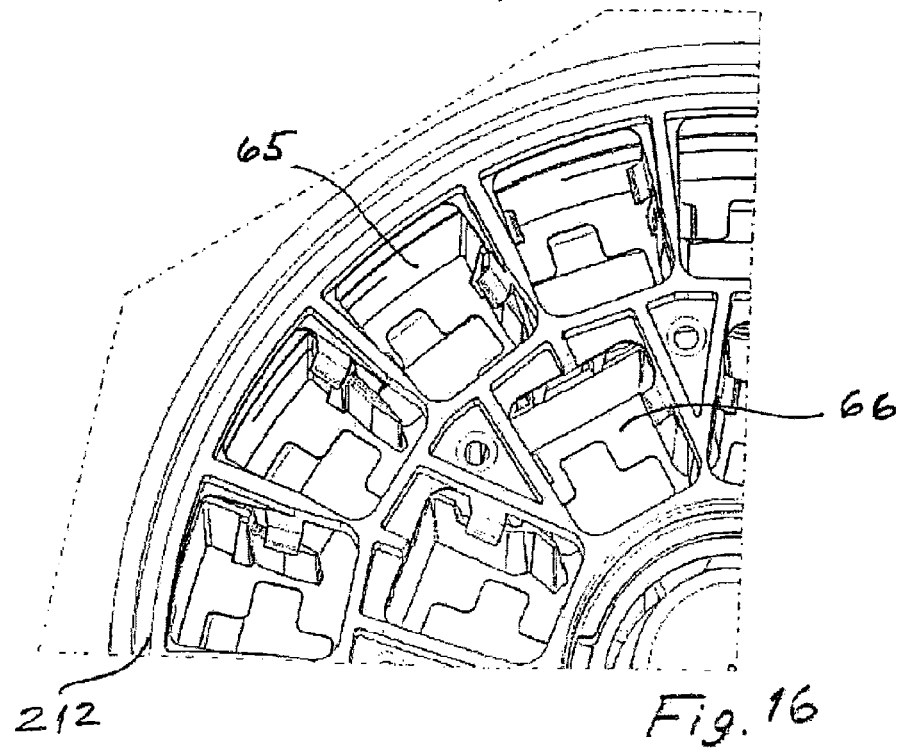
FIG. 16 shows an enlarged view of a portion of FIG. 15.

FIG. 16 shows an enlarged view of a portion of FIG. 15. As can be appreciated from FIGS. 16 and 17 reagent container assembly 61 comprises a housing having two concentric arrays of chambers 65, 66 adapted for receiving reagent containers.

FIG. 17 shows a top view of the conveyor part of the analyzer shown in FIG. 1 and in particular of reagent container assembly 61 before it is loaded with reagent containers.

FIG. 18 shows a perspective view of a reagent container 62.

FIG. 19 shows a cross-sectional view taken along a plane I-I in FIG. 17.

As shown by FIG. 19, reagent container assembly 61 contains a plurality of chambers 65, 66 for receiving reagent containers 63, 64, like reagent container 62 in FIG. 18, each of which contains a specific reagent in liquid form. Each reagent container carries an automatically readable label (not shown), e.g. a barcode label, which identifies the specific reagent contained in the reagent container.

Sample tube area 18 comprises a rack permanently installed in the analyzer. This rack has several cavities 19 and each of these cavities is adapted for receiving a sample tube containing a liquid sample to be analyzed.

Automatic pipetting device 71 is suitable for effecting all pipetting operations in the analyzer, e.g. the pipetting of a sample portion taken from a sample tube in the sample area 18 into a reaction cuvette 31 in conveyor 11 and the pipetting of a reagent volume taken from a reagent container 62 in reagent assembly 61 into a reaction cuvette 31 in conveyor 11. After these pipetting operations the reaction cuvette contains a sample-reagent-mixture.

Automatic pipetting device 71 comprises a removably mounted pipetting needle 72 and a transport device mounted on a rail 73 which extends in the X-direction shown in FIG. 1. This transport device moves the pipetting needle 72 in two ways: along a rectilinear path in the X-direction, e.g. for bringing pipetting needle 72 to a pipetting position, and along a circular path, e.g. when the tip of pipetting needle 72 is immersed in a liquid contained in a reaction cuvette. The latter circular movement of the pipetting needle 72 is achieved by means of an excenter mechanism which is part of the above-mentioned transport device of pipetting needle 72. The excenter mechanism is adapted for moving the tip of pipetting needle along a circular path, but keeping the length axis of pipetting needle 72 in the Z-direction shown in FIG. 1. This circular motion of the pipetting needle is used e.g. for mixing in a reaction cuvette 31 a liquid sample and a reagent which have been pipetted into the reaction cuvette. For this mixing purpose the circular motion of pipetting needle 72 is effected with the tip of pipetting needle 72 partially immersed in the sample-reagent-mixture contained in a reaction cuvette 31.

As shown by FIGS. 1, 13, 15, 17, 23, photometer 21 is located adjacent to conveyor 11 for carrying out photometric measurements of liquid sample-reagent-mixtures contained in reaction cuvettes 31. For this purpose the driving means 22 of conveyor 11 rotate the conveyor step-wise for accurately positioning each reaction cuvette 31 in the optical path 24 of the light beam of photometer 21 so that the latter light beam passes through the center of the lower part of the cuvette which contains the sample-reagent-mixture to be measured with photometer.

Conveyor driving means comprise means for rotating conveyor 11 in a step-wise manner. Conveyor driving means comprise e.g. a belt-drive (not shown) which drives a toothwheel 22 of conveyor 11 and other suitable means for positioning conveyor 11 in accurate angular positions suitable for performing accurate photometrical measurements of the sample-reagent mixture contained in each of the reaction cuvettes 31.

The analyzer shown in FIG. 1 also comprises electrical and electronic components as well as hardware and software for controlling the operation of the analyzer and all components thereof whose operation has to be controlled and coordinated, e.g. the operation of the automatic pipetting device 71, the photometer 21, the management of the samples and reagents present in the analyzer, and the evaluation and display of analysis results and related information.

Example of a Reaction Cuvette

Figure 8:
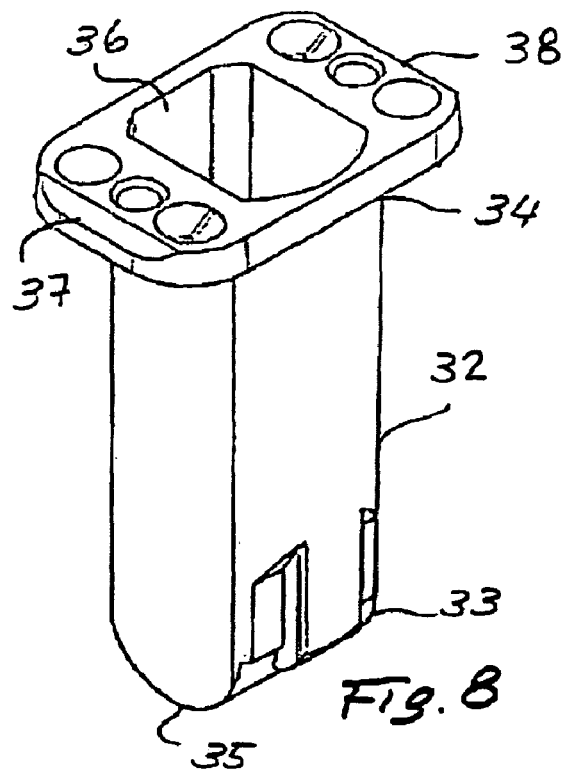
FIG. 8 shows a perspective view of a reaction cuvette 31 of the type which is preferably used with a cuvette holder 41 according to the invention.
Figure 9:
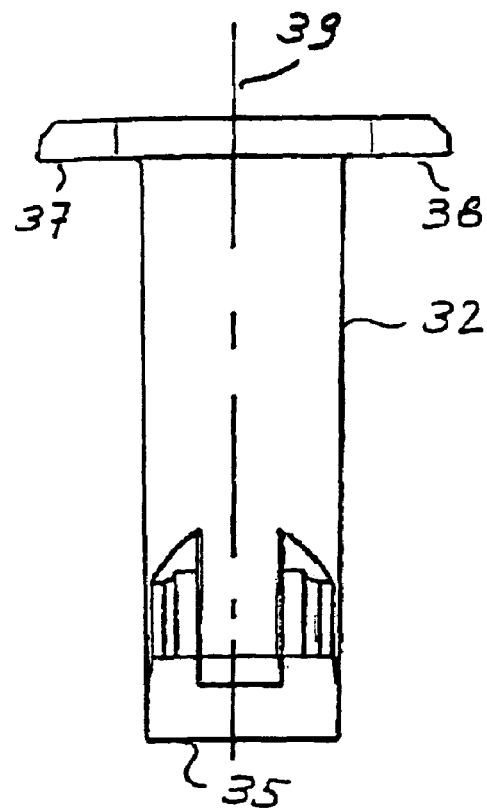
FIG. 9 shows a first side view of reaction cuvette 31 in FIG. 8.
Figure 10:
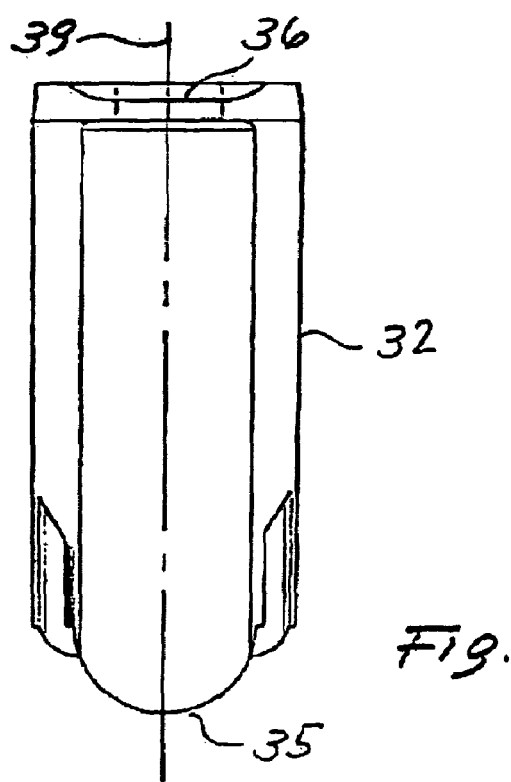
FIG. 10 shows a second side view of reaction cuvette 31 in FIG. 8.

FIG. 8 shows a perspective view of a reaction cuvette 31 of the type which is preferably used with an analyzer of the type described above. FIG. 9 shows a first side view of reaction cuvette 31 in FIG. 8. FIG. 10 shows a second side view of reaction cuvette 31 in FIG. 8. Reaction cuvette 31 is a single-piece, disposable component made by injection molding of a plastic material which is suitable for performing photometric measurements of a sample-reagent mixture contained in reaction cuvette 31.

When a reaction cuvette 31 is inserted in a cavity of conveyor 11 it is in vertical position.

As shown by FIGS. 8 to 10, reaction cuvette 31 has a rectilinear tubular body 32 which extends between a lower end portion 33 and an upper end portion 34 which lie at opposite ends of tubular body 32. Lower end portion 33 is closed by a bottom wall 35. Upper end portion 34 ends in an opening 36 and includes two tongue members 37, 38 adjacent to opening 36 of upper end portion 34. Tongue members 37, 38 extend outwardly from second end portion 34 of the tubular body 32 in opposite directions. Reaction cuvette 31 has a length symmetry axis 39.

Example of a Cuvette Array

An embodiment of a cuvette array suitable for use in an analyzer of the type described above is described hereinafter with reference to FIGS. 4-7.

Figure 4:
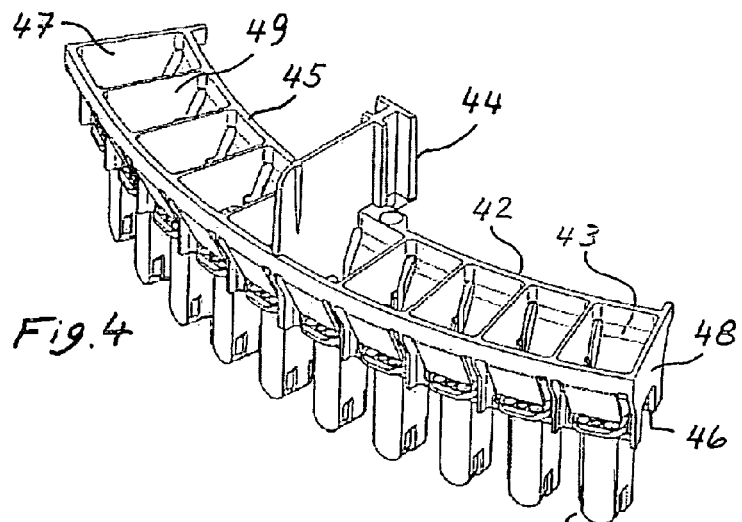
FIG. 4 shows a perspective view of a cuvette array according to the invention comprising a cuvette holder 41 and a plurality of cuvettes 31 of the type shown in FIGS. 8-10.
Figures 6, 7:
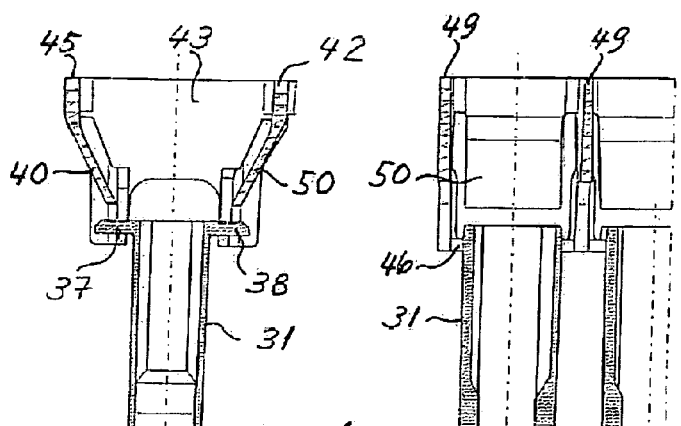
FIG. 6 shows a cross-sectional view taken along a plane C-C in FIG. 5 of a chamber of cuvette holder 41 and of a cuvette 31 held by that chamber.
FIG. 7 shows a cross-sectional view taken along a plane D-D in FIG. 5 of a chamber of cuvette holder 41 and of a cuvette 31 held by that chamber.
Figure 5:
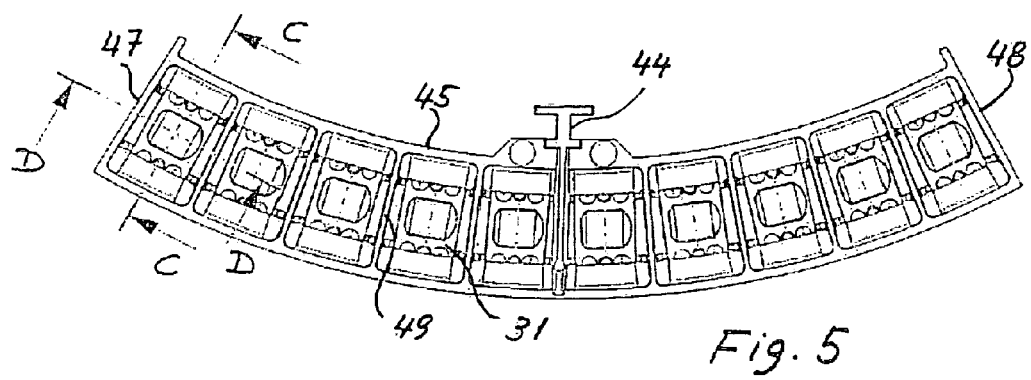
FIG. 5 shows a top plan view of the cuvette array shown in FIG. 4.

FIG. 4 shows a perspective view of a cuvette array according to the invention comprising a cuvette holder 41 and a plurality of cuvettes 31 of the type described above with reference to FIGS. 8-10. FIG. 5 shows a top plan view of the cuvette array shown in FIG. 4. FIG. 6 shows a cross-sectional view taken along a plane C-C in FIG. 5 of a chamber of cuvette holder 41 and of a cuvette 31 held by that chamber. FIG. 7 shows a cross-sectional view taken along a plane D-D in FIG. 5 of a chamber of cuvette holder 41 and of a cuvette 31 held by that chamber.

As can be appreciated in particular from FIG. 4, a cuvette array according to the invention comprises a cuvette holder 41 of the above described type and a plurality of reaction cuvettes 31 of the above described type.

Cuvette holder 41 is configured and dimensioned for loosely holding a plurality reaction cuvettes 31 of the type described above with reference to FIGS. 8 to 10.

Cuvette holder 41 has a body 42 made by injection molding of a plastic material. Body 42 extends along a circular segment and defines an array of chambers 43 arranged along a circular segment. Each of chambers 43 is adapted for receiving and loosely holding the upper end portion 34 of a reaction cuvette 31 and the tongue members 37, 38 of that end portion.

The body 42 of cuvette holder 41 is an integrally made, single-piece, disposable component made by injection molding of a suitable plastic material. Body 42 comprises the following portions:

an upper frame 45,
a lower frame 46,
side walls 47, 48 each of which connect an end of upper frame 45 with one end of lower frame 46,
a plurality of intermediate walls 49 which separate neighboring chambers 43 from each other, and
flexible tongues 40, 50 which extend downwards from the upper frame 45 and which are inclined with respect to a vertical axis passing through the center of a chamber 43.

Each of intermediate walls 49 is radially oriented, i.e. it lies in a plane that passes through the rotation axis 25 of conveyor 11, and connects upper frame 45 with lower frame 46.

The shape and dimensions of frame portions 45 and 46 are such that the array of chambers 43 of cuvette holder 41 closely corresponds to the array of cavities 13 of conveyor 11.

The space available for the upper end portion 34 of a reaction cuvette 31 in each chamber 43 of cuvette holder 41 is delimited by intermediate walls 49 which are the side walls of each chamber 43 and by flexible tongues 40 and 50 which allow the insertion of the reaction cuvette through the upper opening of the chamber, but which prevent removal of the cuvette once the upper end thereof is introduced in chamber 43.

The size of the space available for the upper end portion 34 of a reaction cuvette 31 in each chamber 43 of cuvette holder 41 is chosen large enough to allow displacement of the upper end portion 34 of reaction cuvette in X-, Y-, and Z-direction within chamber 43 and within limits determined by the size of chamber 43. The upper end portion 34 of reaction cuvette 31 and thereby the entire cuvette 31 is thus free to rotate around its length axis 31 within angular limits determined by the size of chamber 43.

In a preferred embodiment, body 42 of cuvette holder 41 further includes a connecting part 44 adapted for connecting body 42 of cuvette holder 41 to conveyor 11 of the analyzer shown in FIG. 1.

As can be appreciated in particular from FIG. 6, the space available for the upper end portion 34 of a reaction cuvette 31 in a chamber 43 of cuvette holder 41 is delimited by intermediate walls 49 which are the side walls of chamber 43 and by flexible tongues 40 and 50 which allow the insertion of the reaction cuvette through the upper opening of chamber 43, but which prevent removal of the cuvette once the upper end portion of the cuvette is introduced into chamber 43.

During the insertion of cuvettes 31 in respective cavities 13 of conveyor 11, are loosely held by cuvette holder 41, but this holder exerts no force or influence on the position each cuvette takes in a cavity 13. The own weight of each cuvette 31 is the only force that acts on it as it is inserted into a cavity 13. The accurate and defined positioning of cuvette 31 in cavity 13 is essentially determined by edges 58 and 59 of the inner surface of bottom wall 56 of cavity 13 and the close match of shape and dimensions of cuvette 31 and the cavity 13.

Example of a Reagent Container Assembly

A reagent container assembly according to the invention is described hereinafter in particular with reference to FIGS. 11-12 and 20-31. Such a reagent assembly is preferably part of an analyzer of the type described above.

Reagent container assembly 61 is adapted for being installed in a cavity 54 of an analyzer as shown by FIG. 14.

As best shown by FIG. 15, reagent container assembly 61 comprises a housing 212 which defines at least one circular array of chambers 65 and/or 66, each of such chambers being adapted for receiving a reagent container 62 (FIG. 18). Housing 212 has an upper opening 256. Reagent container assembly 61 further comprises a cover 211 for closing said upper opening 256 of said housing 212, and locking means arranged within said housing 212.

The above mentioned locking means are adapted for locking cover 211 and for preventing rotation thereof.

The above mentioned locking means are further adapted for locking housing 212 and thereby preventing rotation thereof when the reagent container assembly 61 is removed from its position in said cavity 54 of the analyzer.

The above mentioned locking means are further adapted for cooperating with a pin 224 arranged at the bottom of said cavity 54 of the analyzer when the reagent container assembly 61 is installed in the analyzer, said housing 212 being unlocked by said cooperation and thereby allowed to be rotated within said cavity 54 of the analyzer.

The features of a preferred example of the above mentioned locking means are described hereinafter with reference to FIGS. 20 to 31.

As shown by FIG. 11, reagent container assembly 61 comprises a cover 211 and a housing 212. Housing 212 is composed of an upper part 213 and a lower part 214 which are permanently connected with each other by means of a bayonet coupling.

Cover 211 has two openings 241 and 242 for pipetting operations allowing to take reagent volumes from reagent containers 62 contained in housing 212 of reagent container assembly 61.

Cover 211 has two openings 243 and 244 intended to be gripped by a user for holding and/or lifting reagent container assembly 61.

Cover 211 has an opening 245 which allows removal of a reagent container 62 from housing 212 or insertion of a reagent container 62 into a chamber of housing 212 when the control system of the analyzer puts the conveyor 11 in a position that allows such an operation.

As shown by FIG. 11, cover 211 has an arrow head marker 254 on it and the upper part 213 of housing 212 has also an arrow head marker 255 on it. FIG. 11 shows the position of arrow head markers 254 and 255 which is required for installing reagent container assembly 61 in the analyzer and for removing it therefrom.

Figure 12:
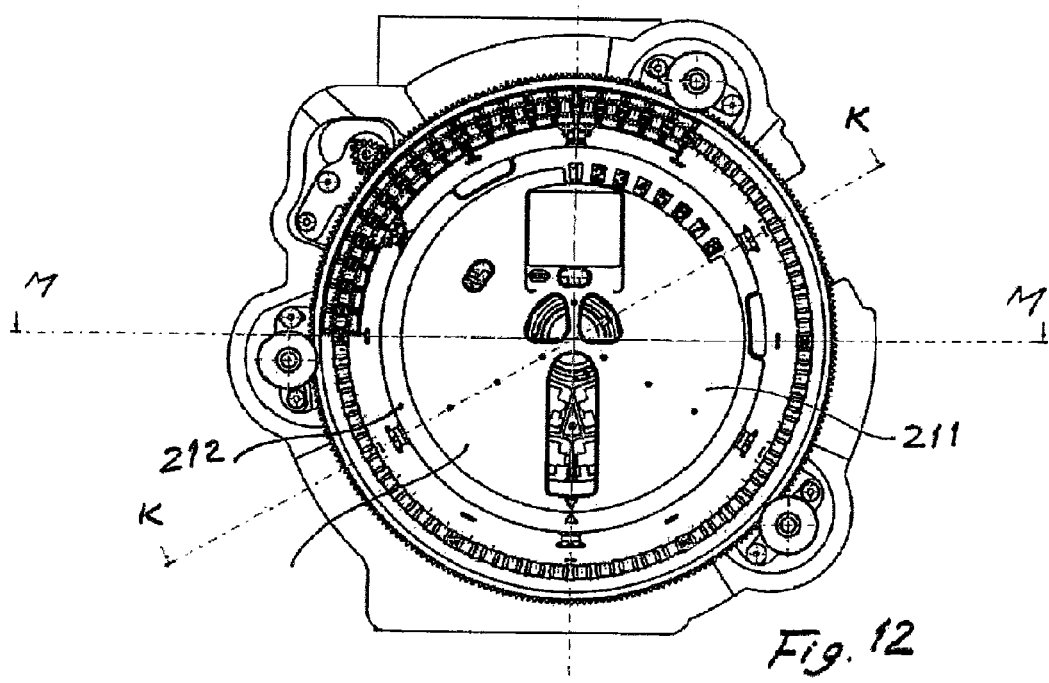
FIG. 12 shows a top view of the conveyor part of the analyzer shown in FIG. 1 when reagent container assembly 61 is installed in the analyzer.
Figure 20:
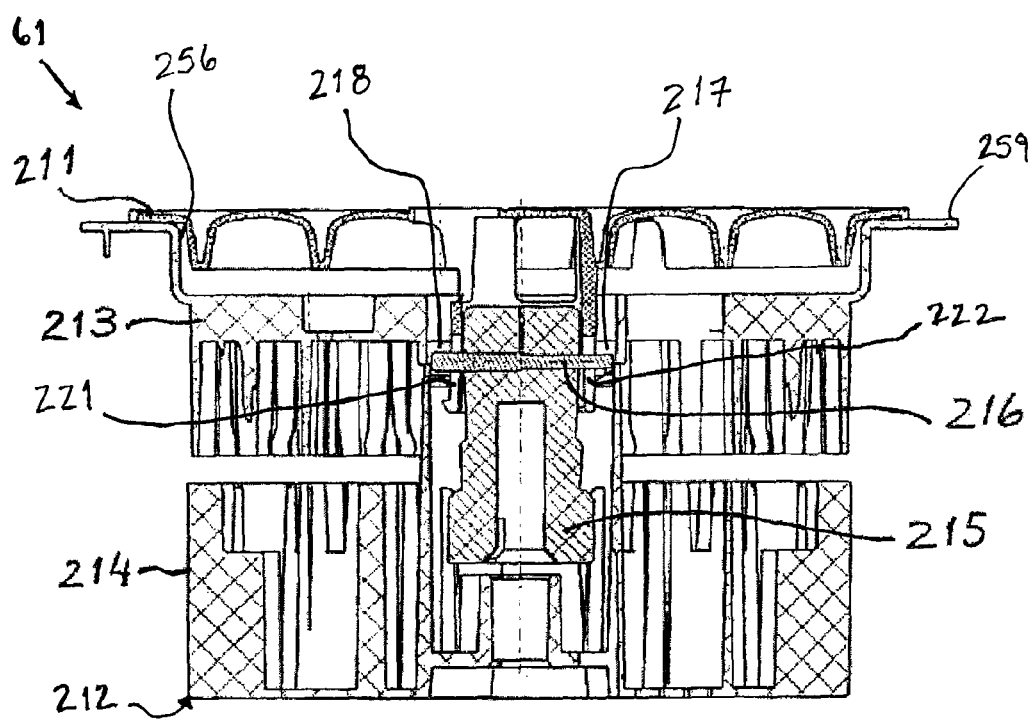
FIG. 20 shows a first cross-sectional view of reagent container assembly 61 taken along a plane K-K in FIG. 12. In this view the cover 211 rests on the top edge of the upper part 213 of housing 212 of reagent container assembly 61.

FIG. 20 shows a first cross-sectional view of reagent container assembly 61 taken along a plane K-K in FIG. 12. In this view the cover 211 rests on a top edge 259 of the upper part 213 of housing 212 of reagent container assembly 61.

As shown by FIG. 20, reagent container assembly 61 further comprises the following additional parts which are arranged within housing 212 and which are part of a locking mechanism: a locking sleeve 215 and a locking pin 216.

Figure 21:
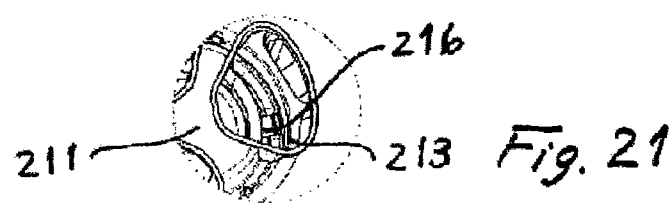
FIG. 21 shows a partial perspective view showing the position of locking pin 216 in the locked position of the housing 212.

FIG. 21 shows a partial perspective view showing the position of locking pin 216 in the locked position of the housing 212.

FIGS. 20 and 21 show the relative positions of the different parts of the reagent container assembly 61 with respect to each other when the reagent container assembly is removed from its usual position in the analyzer.

FIG. 20 shows the relative positions of the different parts of the reagent container assembly with respect to each other when the reagent container assembly it rests e.g. on a table in a parked state.

In the state of the reagent container assembly shown in FIG. 20, cover 211 rests on the upper part 213 of housing 212, locking sleeve 215 is held by its own weight in the position shown in FIG. 20, and the end portions of locking pin 216 are in respective recesses 217 and 218 of upper part 213 of housing 212. The latter recesses 217 and 218 are on the one hand radial guides for the end portions of locking pin 216 and on the other hand they define the height at which locking pin 216 is located. FIG. 21 is an enlarged perspective view showing the relative position of locking pin 216 when the reagent container assembly is in the parked state shown in FIG. 20.

In the state of the reagent container assembly shown in FIG. 20, cover 211 cannot be rotated around the vertical central axis shown in FIG. 20, because two guide elements 221 and 222 of cover 211 connect it with locking pin 216 and this connection keeps cover 211 in a fixed angular position.

In the state of the reagent container assembly shown in FIG. 20, locking sleeve 215 is connected by locking pin 216 with upper part 213 of housing 212. In the state of the reagent container assembly shown in FIG. 20, cover 211 is also connected by locking pin 216 with upper part 213 of housing 212.

FIG. 21 shows how locking pin 216 is locked in the recesses 217, 218 of upper part 213 of housing 212.

As can be appreciated from FIG. 20, the cross-sections of the opposite end portions of locking pin 216 are different and the sizes of recesses 217 and 218 are adapted thereto. This arrangement defines only one possible position of locking pin 216 with respect to upper part 213 of housing 212 when the end portions of locking pin 216 are lodged in recesses 217 and 218 respectively. In the example shown by FIG. 20, the end portion of locking pin 216 on the right side has a diameter d=3 mm h8 and is lodged in recess 217 which has a diameter of 3 mm, whereas the end portion of locking pin 216 on the left side has a diameter D=4 mm h8 and is lodged in recess 218 which has a diameter of 4 mm.

Figure 22:
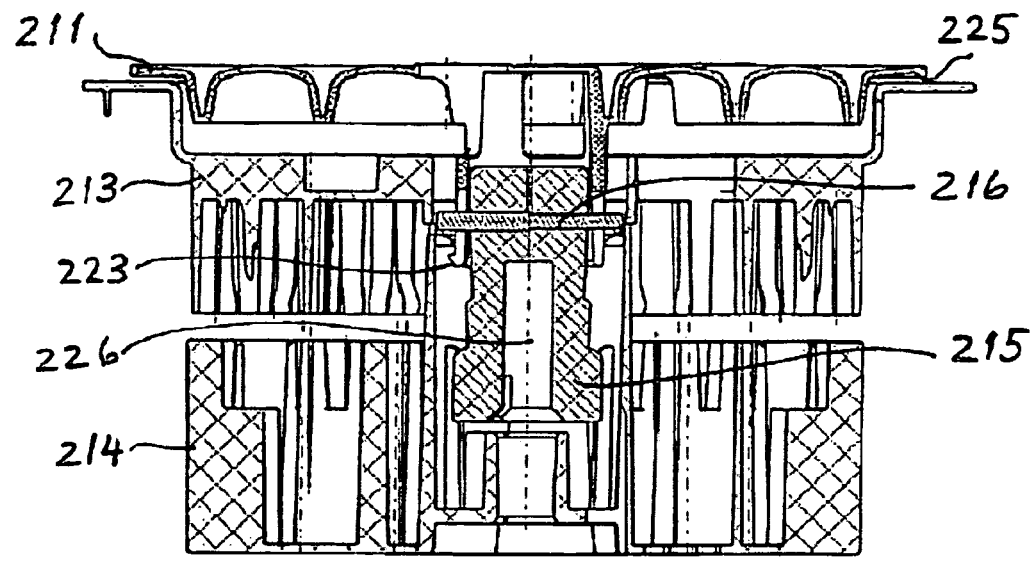
FIG. 22 shows a second cross-sectional view of reagent container assembly 61 taken along a plane K-K in FIG. 12. In this view the cover 211 is separated by an air gap from the top edge of the upper part 213 of housing 212 of reagent container assembly 61.

FIG. 22 shows a second cross-sectional view of reagent container assembly 61 taken along a plane K-K in FIG. 12.

FIG. 22 shows the relative positions of the different parts of the reagent container assembly with respect to each other when the reagent container assembly is carried by hand by a user.

In the state of the reagent container assembly shown in FIG. 22, cover 211 is lifted off and thereby separated from the upper part 213 of housing 212 by an air gap 225 of about 1-2 mm.

When a user lifts reagent container assembly 61 by gripping cover 211 at suitable openings 243, 244 thereof, cover 211 is initially lifted off and thereby separated from the upper part 213 of housing 212 until a hook 223 of cover 211 contacts upper part 213 of housing 212. When cover 211 reaches this position the whole assembly is lifted by the user. The above described locking of the cover 211 and the housing 212 remains however unchanged, because all above mentioned parts remain locked and cannot be rotated with respect to each other.

Figure 23:
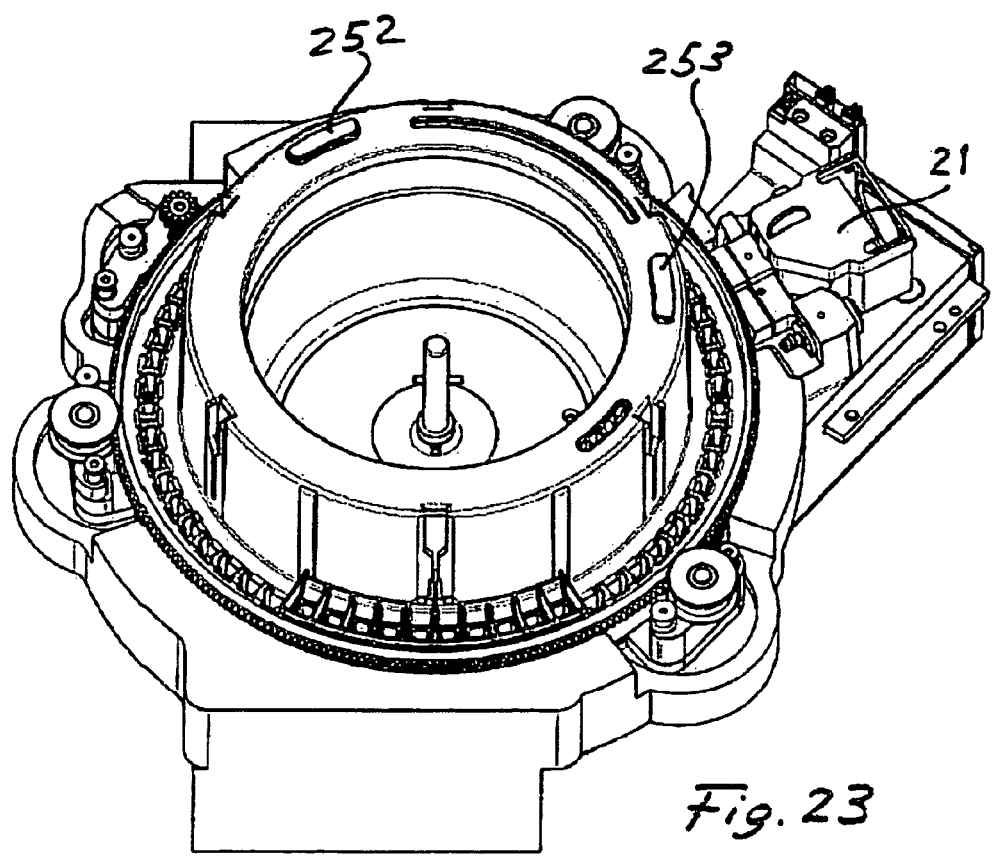
FIG. 23 shows a perspective view of conveyor 11 in FIG. 1.

FIG. 23 shows a perspective view of conveyor 11 in FIG. 1.

Figure 26:
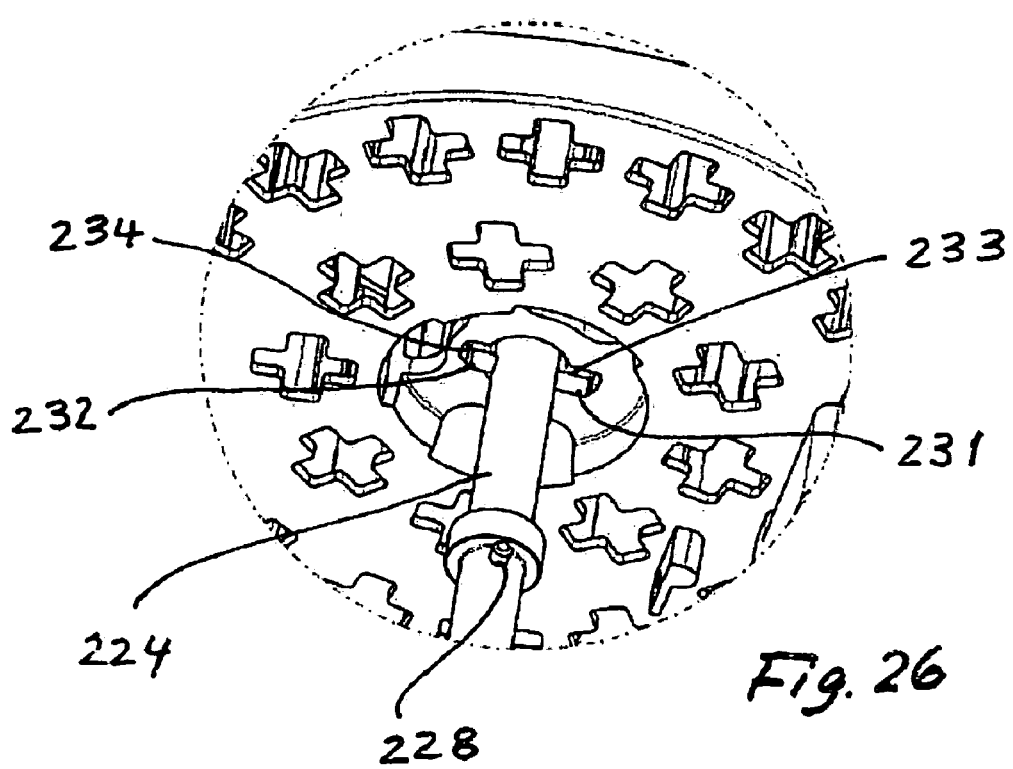
FIG. 26 shows a partial perspective view of the upper part of bolt 224 in FIG. 23, when projections 231 and 232 of that upper part pass through corresponding recesses of lower part 214 of housing 212.

As shown by FIGS. 14, 23 and 26, the lower part of a bolt 224 is mounted in an opening of the bottom wall 52 of bucket 51.

Figure 24:
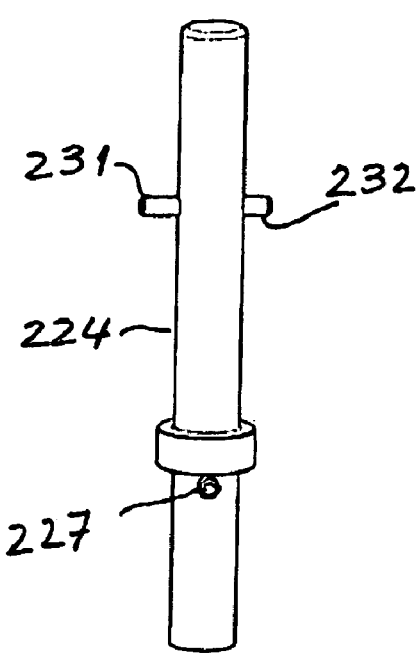
FIG. 24 shows a first side view of bolt 224 in FIG. 23.
Figure 25:
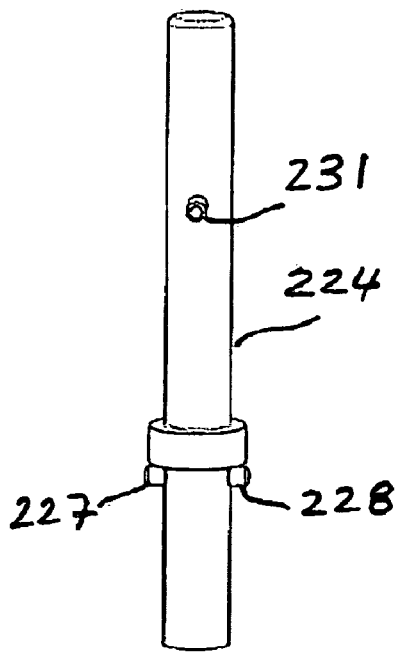
FIG. 25 shows a second side view of bolt 224 in FIG. 23.

FIGS. 24 and 25 show two different side views of bolt 224. As shown by FIGS. 24 and 25 the lower part of bolt 224 has projections 226 and 227 which are inserted in corresponding recesses of the bottom wall 52 of bucket 51 and thereby define the fixed angular position of bolt 224 with respect to bucket 51.

As shown by FIGS. 24 and 25 the upper part of bolt 224 has projections 231 and 232 which have different lengths, projection 231 being longer than projection 232.

In the interior of lower part 214 of housing 212 there are two recesses 233, 234 for receiving projections 231 and 232, and recesses 233, 234 have depths corresponding to the respective lengths of projections 231 and 232. This ensures that housing 212 can only be connected to bolt 224 and introduced into conveyor 11 at a single, defined angular position of the reagent container assembly 61 with respect to conveyor 11.

FIG. 26 shows a partial perspective view of the upper part of bolt 224 in FIG. 23. When projections 231 and 232 of that upper part pass through the corresponding recesses 233 and 234 of lower part 214 of housing 212, lower part 214 is free to rotate with respect to bolt 224 which is fixedly mounted in the bottom wall of bucket 51.

In order to install reagent container assembly 61 in the analyzer shown in FIG. 1, assembly 61 is introduced in chamber 54 of bucket 51 with an angular position at which projections 231 and 232 of bolt 224 suitably enter the corresponding recesses of lower housing part 214 and allow bolt 224 to enter into a recess 226 (shown in FIG. 22) of locking sleeve 215 and take the position shown by FIG. 27. When reagent container assembly 61 reaches this position the upper edge of upper part 213 of housing 212 comes to rest on the upper edge of second ring shaped body 14 of conveyor 11.

FIG. 28 shows a first perspective view of the cover 211 and of locking sleeve 215 in FIG. 27. FIG. 28 shows that with assembly 61 in the position shown in FIG. 27, locking pin 216 is inserted between guides 219 which are part of cover 211 and thereby keep cover 211 locked. Cover 211 is thus kept in the position shown with respect to locking sleeve 215 also after insertion of reagent container assembly 61 in cavity 54 of the conveyor, i.e. after installation of assembly 61 in the analyzer.

Figure 31:
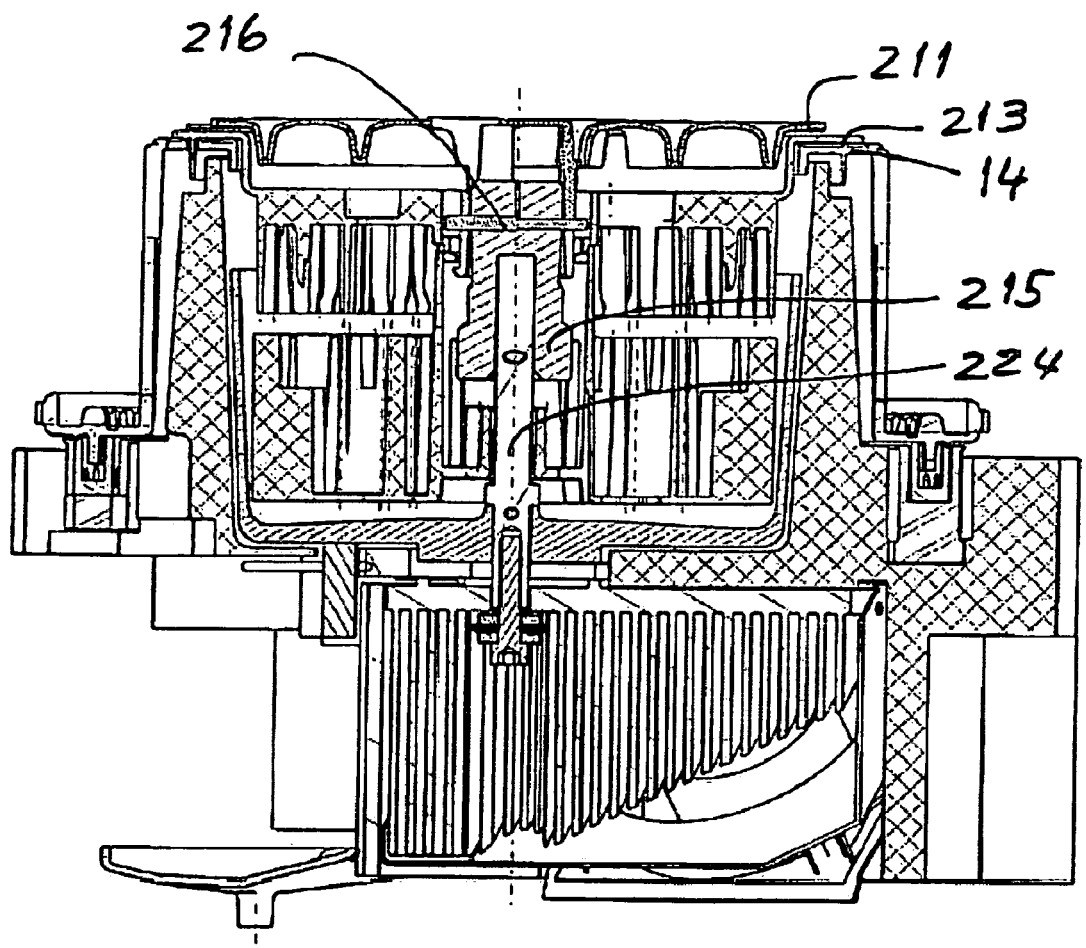
FIG. 31 shows a fourth cross-sectional view of reagent container assembly 61 taken along a plane K-K in FIG. 12. In this view reagent container assembly 61 is in unlocked position.

FIG. 29 shows a second perspective view of the cover 211, locking sleeve 215 and bolt 224 in FIG. 27. FIG. 28 shows that with reagent container assembly 61 in the position shown in FIG. 27, projections 231 and 232 are inserted in respective recesses 235 and 236 of locking sleeve 215. This prevents rotation of cover 211 with respect to housing 212 of reagent container assembly 61. Housing 212 (its upper and lower parts 213, 214) are however allowed to slide downwards and this movement brings locking pin out of its locked position in upper housing part 213, and thereby housing 212 becomes free to be rotated by rotation of conveyor 11 on which housing part 213 rests upon. FIG. 31 shows the position of locking sleeve 215 and locking pin 216 when this state is reached.

In the position shown in FIG. 31 reagent container assembly 61 rests on second rings shaped body 14 of conveyor 11. In this position, projections 252, 253 in the upper edge of body 14 engage corresponding recesses 257 and 258 (FIG. 11) of housing 212 of reagent container assembly 61 and thereby connect this housing to conveyor 11. By stepwise rotation of conveyor 11, housing 212 and thereby the array of reagent containers in that housing can thus be rotated with respect to cover 211, and this makes possible to access anyone of the reagent containers for taking a reagent volume with the automatic pipetting device 71. Cover 211 of reagent container assembly 61 remains stationary.

Although preferred embodiments of the invention have been described using specific terms, such description is for illustrative purposes only, and it is to be understood that changes and variations may be made without departing from the spirit or scope of the following claims.

What is claimed is:

1. A reagent container assembly for holding reagent containers and for installation in a substantially cylindrical cavity of an analyzer, the cavity having a bolt arranged at a bottom center thereof, said reagent container assembly comprising:

a housing defining at least one circular array of chambers which receive the reagent containers, said housing having a top edge of an upper part defining an opening above said chambers;

a cover for said upper opening of said housing, said cover having only a single opening configured to allow removal of a reagent container from one of the chambers in the housing or insertion of the reagent container into one of the chambers of housing; and locking means arranged within said housing, said locking means comprising a locking sleeve and a locking pin, said locking means locks said cover at all times both to prevent rotation of the cover with respect to the analyzer when the reagent container assembly is positioned in said cavity of the analyzer, and to prevent rotation of said cover with respect to said housing when the reagent container assembly is removed from its position in said cavity of the analyzer, and said locking means cooperates with the bolt arranged at the bottom center of said cavity of the analyzer when the reagent container assembly is installed in the analyzer to unlock said housing by said cooperation and to allow rotation of said housing with respect to said cover within said cavity of the analyzer.

2. The reagent container assembly according to claim 1, wherein said housing further defines a recess in which said locking pin in a first state seats to lock the cover relative to the housing, and in a second state unseats from the recess to permit the housing to rotate relative to the cover to allow the array of chambers to rotate within the cavity of the analyzer.

3. The reagent container assembly according to claim 1, wherein the housing has recesses which accommodate projections of the analyzer.

4. The reagent container assembly according to claim 1, wherein the cover has two additional openings allowing taking of reagent volumes from reagent containers contained in the housing of reagent container assembly.

5. The reagent container assembly according to claim 4, wherein the cover has two further openings intended to be gripped by a user for lifting the reagent container assembly.

6. The reagent container assembly according to claim 1, wherein when the reagent container assembly is removed from its position in said cavity of the analyzer the cover rests on the housing of reagent container assembly.

7. The reagent container assembly according to claim 6, wherein the cover rests on a top edge of an upper part of housing of reagent container assembly.

8. The reagent container assembly according to claim 1, wherein when the reagent container assembly is lifted from the cavity of the analyzer the cover separates from an upper part of housing by an air gap, wherein the cover and housing remain locked and cannot rotate with respect to each other.

9. The reagent container assembly according to claim 1, wherein the cover has a first arrow head marker and an upper part of housing has a second arrow head marker, wherein alignment of the first and second arrow head markers together is required for installing the reagent container assembly in the analyzer and for removing it therefrom.

10. The reagent container assembly according to claim 1, wherein when the reagent container assembly is removed from its position in the cavity of the analyzer, the locking sleeve is held by its own weight and end portions of the locking pin are in respective recesses of an upper part of the housing, thereby defining a park state.

11. The reagent container assembly according to claim 10, wherein the recesses of the upper part of the housing are both radial guides for end portions of the locking pin and define the height at which the locking pin is located in the parked state.

12. The reagent container assembly according to claim 1, wherein opposite end portions of the locking pin are different in size.

13. The reagent container assembly according to claim 1, wherein the locking pin is inserted between guides which are part of the cover.

14. The reagent container assembly according to claim 1, wherein the housing has recesses, and the locking pin and the recesses are arranged to define only one possible position in which the locking pin lodge in the recesses.

15. The reagent container assembly according to claim 1, wherein the housing has recesses in a lower part of housing which receive projections of the bolt to ensure that housing can only be connected to bolt at a single, defined angular position of the reagent container assembly with respect to a conveyor of the analyzer.

* * * * *